United States Patent
Ikeda et al.

(12) 
(10) Patent No.: US 6,489,046 B1
(45) Date of Patent: Dec. 3, 2002

(54) ORGANIC ELECTROLUMINESCENCE DEVICE

(75) Inventors: Hidetsugu Ikeda, Chiba-ken (JP); Hidetoshi Koga, Chiba-ken (JP); Yoshinori Yanagisawa, Chiba-ken (JP); Sanae Tagami, Chiba-ken (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 09/675,200

(22) Filed: Sep. 29, 2000

(30) Foreign Application Priority Data

Sep. 30, 1999 (JP) .......................... 11-279463

(51) Int. Cl.$^7$ .................. H05B 33/12; C09K 11/06
(52) U.S. Cl. ................. 428/690; 428/917; 313/504; 313/506; 252/301.16
(58) Field of Search ................ 428/690, 917; 313/504, 506; 252/301.16

(56) References Cited

U.S. PATENT DOCUMENTS

| 5,151,629 A | * | 9/1992 | VanSlyke ............... 313/504 |
| 5,281,489 A | * | 1/1994 | Mori et al. ............. 428/690 |
| 6,203,933 B1 | * | 3/2001 | Nakaya et al. .......... 428/690 |

FOREIGN PATENT DOCUMENTS

JP  8-311442  * 11/1996

\* cited by examiner

Primary Examiner—Marie Yamnitzky
(74) Attorney, Agent, or Firm—Oblon, Spivak, McClelland, Maier & Neustadt, P.C.

(57) ABSTRACT

An organic electroluminescence device which exhibits an excellent purity of color and a high efficiency of light emission, has a long life and emits reddish light and a novel compound having these characteristics. The organic electroluminescence device comprises an organic layer disposed between at least one pair of electrodes, wherein the organic layer comprises a compound represented by general formula [1]:

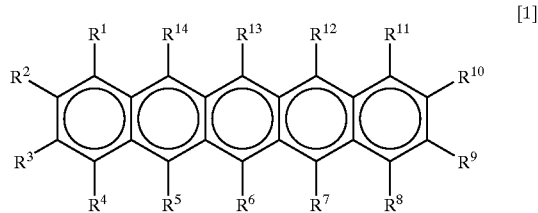

wherein $R^1$ to $R^{14}$ each independently represent hydrogen atom, an alkyl group having 1 to 10 carbon atoms, an aryloxy group having 6 to 20 carbon atoms, an arylalkyl group having 6 to 20 carbon atoms, an aryl group having 6 to 30 carbon atoms, an arylamino group having 6 to 30 carbon atoms, an alkylamino group having 2 to 20 carbon atoms or an arylalkylamino group having 6 to 30 carbon atoms, the groups being substituted or unsubstituted; and at least one pair of R among $R^1$ to $R^{14}$ which are adjacent to each other do not represent hydrogen atom but represent groups which form a cyclic structure in combination.

11 Claims, No Drawings

ORGANIC ELECTROLUMINESCENCE DEVICE

TECHNICAL FIELD

The present invention relates to an organic electroluminescence device which is used as a light source such as a planar light emitting member of televisions and a back light of displays, exhibits an excellent purity of color and a high efficiency of light emission, has a long life and emits reddish light and to a novel compound having these characteristics.

BACKGROUND ART

Electroluminescence (referred to as EL, hereinafter) devices using organic compounds are expected to be used for inexpensive full color display devices of the solid light emission type which can display a large area and development thereof has been actively conducted. In general, an EL device is constituted with a light emitting layer and a pair of electrodes faced to each other at both sides of the light emitting layer. When a voltage is applied between the electrodes, electrons are injected at the side of the cathode and holes are injected at the side of the anode. The electrons are combined with the holes in the light emitting layer and an excited state is formed. When the excited state returns to the ground state, the energy is emitted as light.

Although the practical application of organic EL devices has started recently, devices for full color displays are still under development. In particular, a material for organic EL devices which exhibits an excellent purity of color and a high efficiency of light emission, has a long life and emits reddish light has been desired.

In an attempt to satisfy the above desire, a device emitting red light in which a derivative of naphthacene or pentacene is added to a light emitting layer is disclosed in Japanese Patent Application Laid-Open No. Heisei 8(1996)-311442. Although this device exhibits an excellent purity of red light, the device exhibits an efficiency of light emission as low as 0.7 lm/W and has an insufficient average life which is shorter than 150 hours. An average life of at least several thousand hours is necessary for practical applications. A device in which a compound derived from dicyanomethylene (DCM) is added to a light emitting layer is disclosed in Japanese Patent Application Laid-Open No. Heisei 3(1991)-162481. However, this device exhibits an insufficient purity of red light.

DISCLOSURE OF THE INVENTION

The present invention has been made to overcome the above problems and has an object of providing an organic EL device which exhibits an excellent purity of color and a high efficiency of light emission, has a long life and emits reddish light and a novel compound having these characteristics.

As the result of extensive studies by the present inventors to develop the organic EL device having the above advantageous properties, it was found that the object can be achieved by using a compound represented by the following general formula [1], [2] or [2'] as the light emitting material.

The organic EL device of the present invention comprises an organic layer disposed between at least one pair of electrodes, wherein the organic layer comprises a compound represented by general formula [1]:

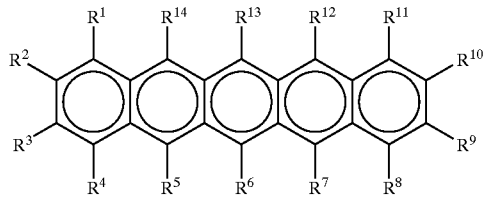

wherein $R^1$ to $R^{14}$ each independently represent hydrogen atom, an alkyl group having 1 to 10 carbon atoms, an aryloxy group having 6 to 20 carbon atoms, an arylalkyl group having 6 to 20 carbon atoms, an aryl group having 6 to 30 carbon atoms, an arylamino group having 6 to 30 carbon atoms, an alkylamino group having 2 to 20 carbon atoms or an arylalkylamino group having 6 to 30 carbon atoms, the groups being substituted or unsubstituted; and at least one pair of R among $R^1$ to $R^{14}$ which are adjacent to each other do not represent hydrogen atom but represent groups which form a cyclic structure in combination.

The organic EL device of the present invention may also comprise an organic layer disposed between at least one pair of electrodes, wherein the organic layer comprises a compound represented by general formula [2]:

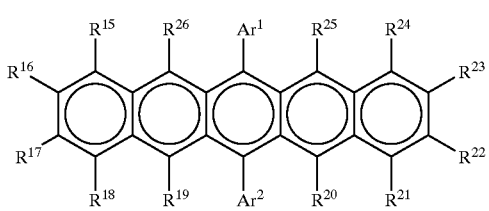

wherein $R^{15}$ to $R^{26}$ each independently represent hydrogen atom, an alkyl group having 1 to 10 carbon atoms, an aryloxy group having 6 to 20 carbon atoms, an arylalkyl group having 6 to 20 carbon atoms, an aryl group having 6 to 30 carbon atoms, an arylamino group having 6 to 30 carbon atoms, an alkylamino group having 2 to 20 carbon atoms or an arylalkylamino group having 6 to 30 carbon atoms, the groups being substituted or unsubstituted; at least one pair of R among $R^{15}$ to $R^{26}$ which are adjacent to each other do not represent hydrogen atom but represent groups which form a cyclic structure in combination; and $Ar^1$ and $Ar^2$ represent a substituted or unsubstituted aryl group having 6 to 30 carbon atoms or a substituted or unsubstituted heterocyclic group having 5 to 30 carbon atoms.

The novel organic compound emitting red light which is useful for the organic EL device of the present invention is represented by general formula [2']:

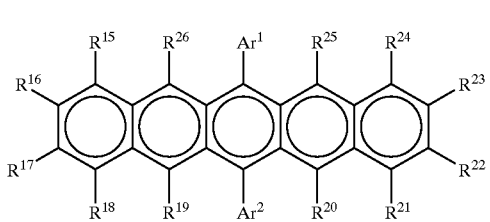

wherein $R^{15}$ to $R^{26}$ and $Ar^1$ and $Ar^2$ are as defined above in general formula [2], excluding the case in which $Ar^1$ and $Ar^2$ both represent phenyl group.

THE MOST PREFERRED EMBODIMENT TO CARRY OUT THE INVENTION

In the organic EL device of the present invention, an organic layer is disposed between at least one pair of electrodes and the organic layer comprises at least one of the compounds represented by general formula [1] and general formula [2] shown above.

$R^1$ to $R^{14}$ in general formula [1] shown above each independently represent hydrogen atom, an alkyl group having 1 to 10 carbon atoms, an aryloxy group having 6 to 20 carbon atoms, an arylalkyl group having 6 to 20 carbon atoms, an aryl group having 6 to 30 carbon atoms, an arylamino group having 6 to 30 carbon atoms, an alkylamino group having 2 to 20 carbon atoms or an arylalkylamino group having 6 to 30 carbon atoms. These groups may be substituted. At least one pair of R among $R^1$ to $R^{14}$ which are adjacent to each other do not represent hydrogen atom but represent groups which form a cyclic structure in combination.

It is preferable that $R^1$ to $R^{14}$, except the pair of R which are adjacent to each other and represent groups forming a cyclic structure in combination, represent an alkyl group, an aryloxy group, an arylalkyl group, an aryl group, an arylamino group, an alkylamino group or an arylalkylamino group having 6 to 30 carbon atoms.

$R^{15}$ to $R^{26}$ in general formula [2] shown above each independently represent hydrogen atom, an alkyl group having 1 to 10 carbon atoms, an aryloxy group having 6 to 20 carbon atoms, an arylalkyl group having 6 to 20 carbon atoms, an aryl group having 6 to 30 carbon atoms, an arylamino group having 6 to 30 carbon atoms, an alkylamino group having 2 to 20 carbon atoms or an arylalkylamino group having 6 to 30 carbon atoms. These groups may be substituted. At least one pair of R among $R^{15}$ to $R^{26}$ which are adjacent to each other do not represent hydrogen atom but represent groups which form a cyclic structure in combination. $Ar^1$ and $Ar^2$ represent a substituted or unsubstituted aryl group having 6 to 30 carbon atoms or a substituted or unsubstituted heterocyclic group having 5 to 30 carbon atoms.

The novel organic compound emitting red light which is useful for the organic EL device of the present invention is represented by general formula [2'] shown above.

In general formula [2'], $R^{15}$ to $R^{26}$, $Ar^1$ and $Ar^2$ are as defined above in general formula [2], excluding the case in which $Ar^1$ and $Ar^2$ both represent phenyl group.

The above organic layer comprises a light emitting layer which comprises at least one of the compounds represented by general formula [1] and general formula [2] shown above.

It is preferable that the light emitting layer comprises 0.1 to 20% by mole and more preferably 1 to 5% by mole of at least one of the compounds represented by general formula [1] and general formula [2].

The light emitting layer may be a light emitting layer having an electron transporting property. A layer of an inorganic compound may be disposed between the organic layer and the electrode.

The organic EL device of the present invention emits reddish light.

Examples of the compounds represented by general formula [1], general formula [2] and general formula [2'] of the present invention include (A-1) to (A-26) which are shown in the following. However, the present invention is not limited to these compounds shown as the examples. In the formulae shown in the following, Me means methyl group.

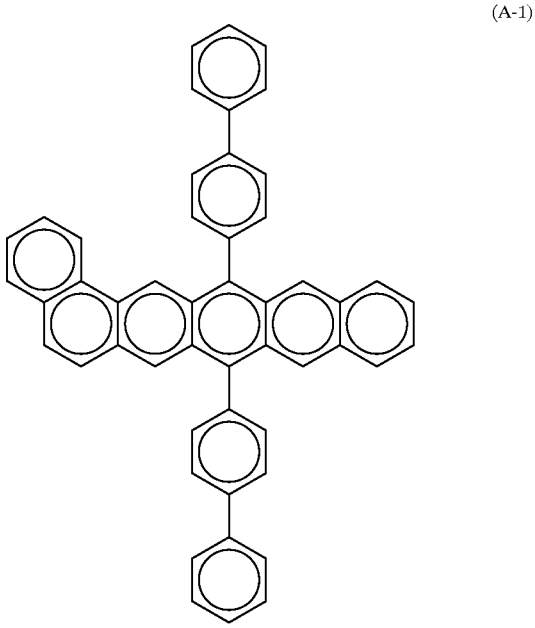

(A-1)

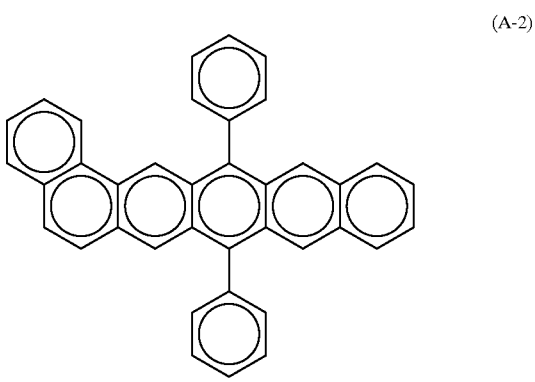

(A-2)

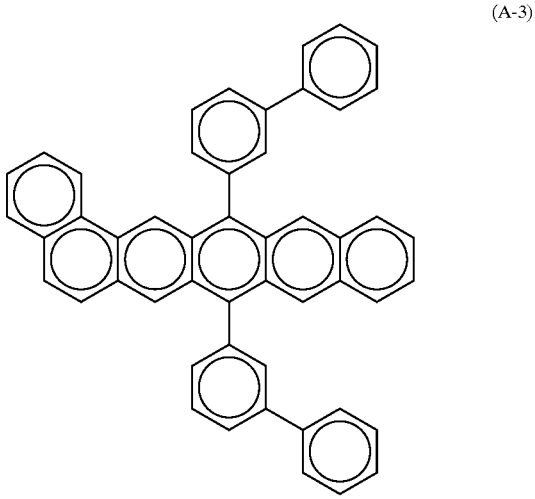

(A-3)

(A-4)
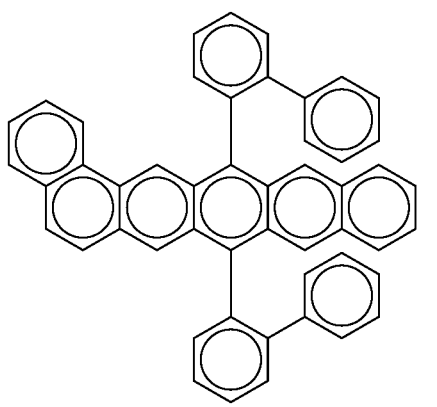
(A-5)
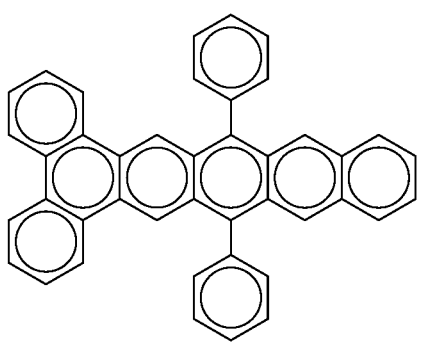
(A-6)
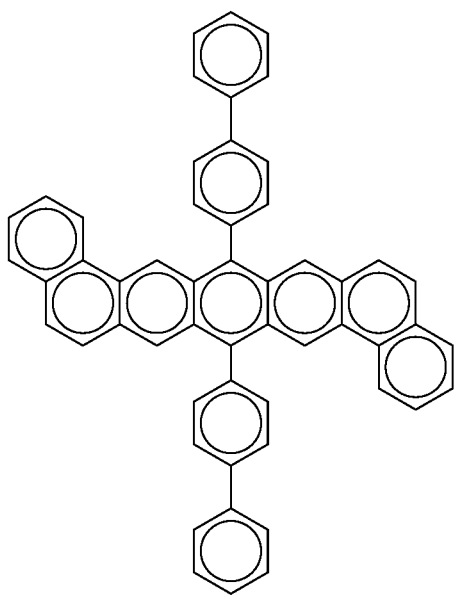
(A-7)
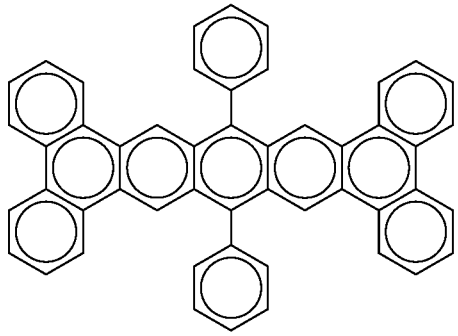
(A-8)
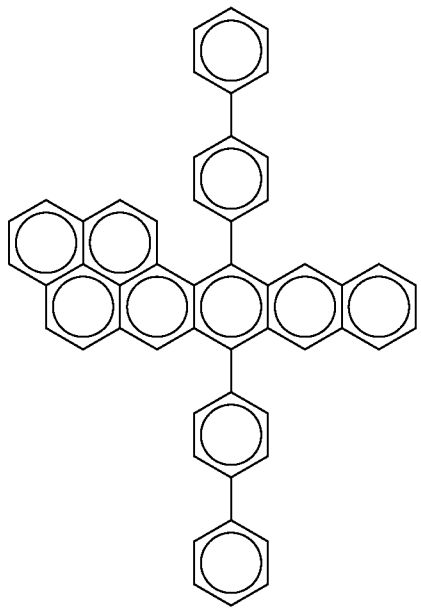
(A-9)
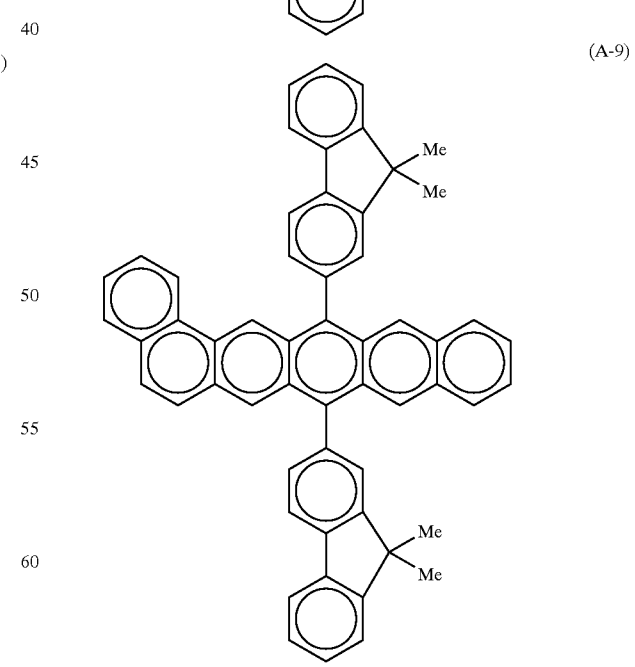

(A-10)
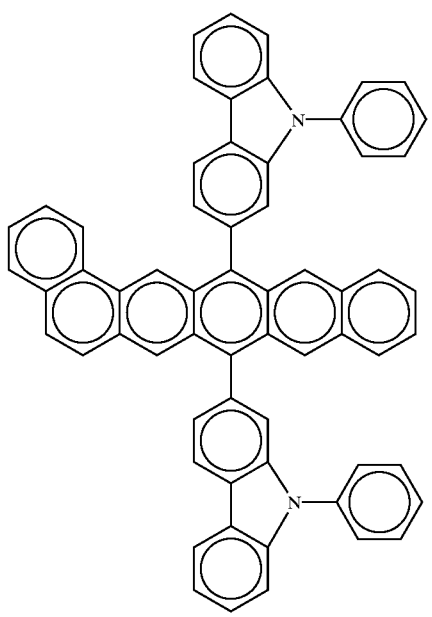
(A-13)
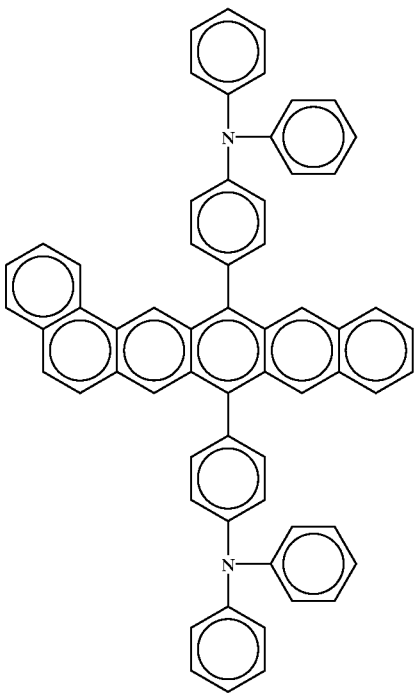
(A-11)
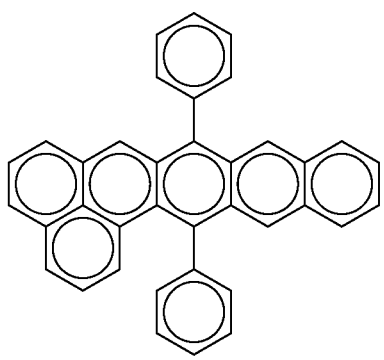
(A-14)
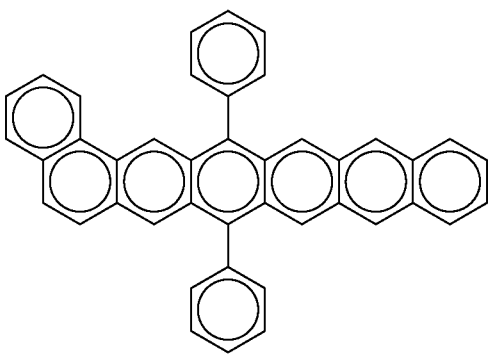
(A-12)
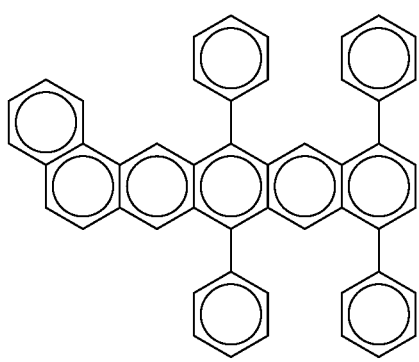
(A-15)
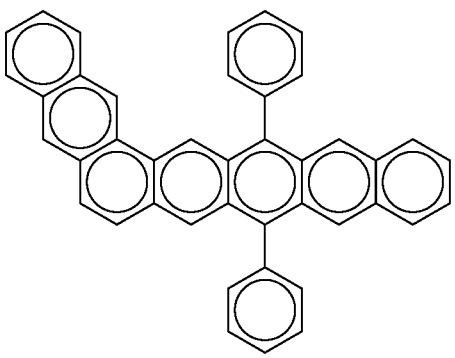

(A-16)
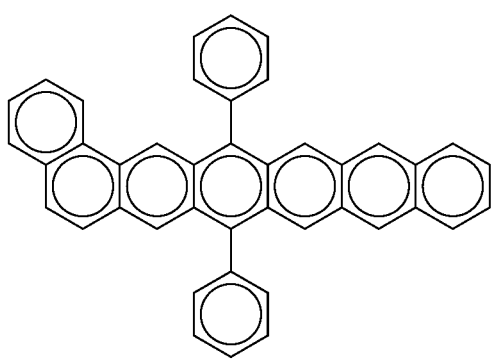
(A-17)
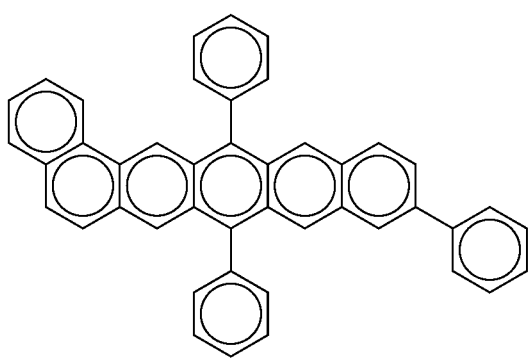
(A-18)
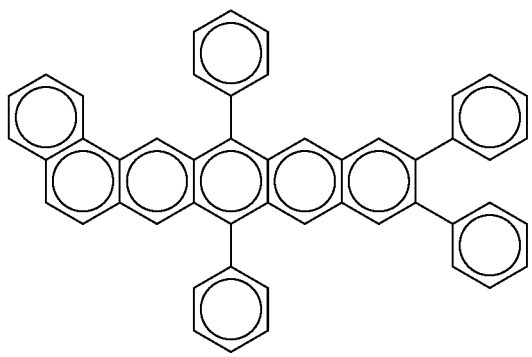
(A-19)
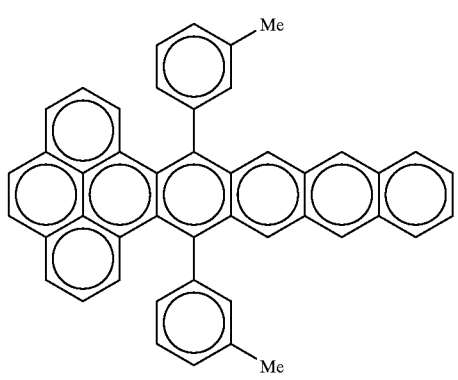
(A-20)
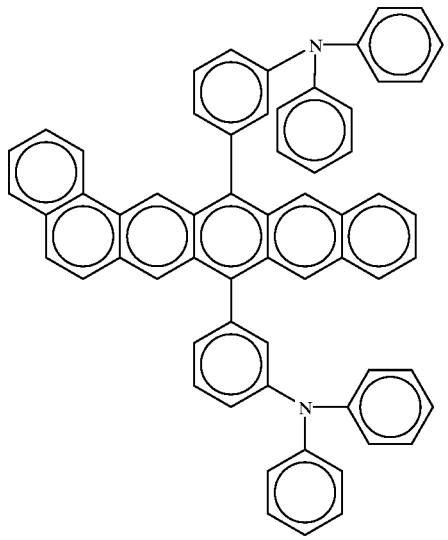
(A-21)
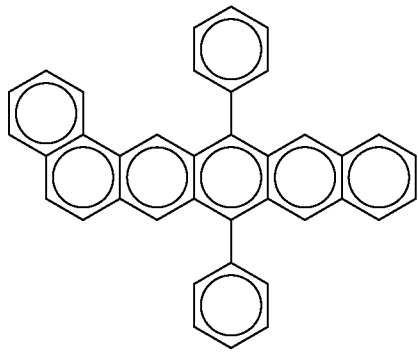
(A-22)
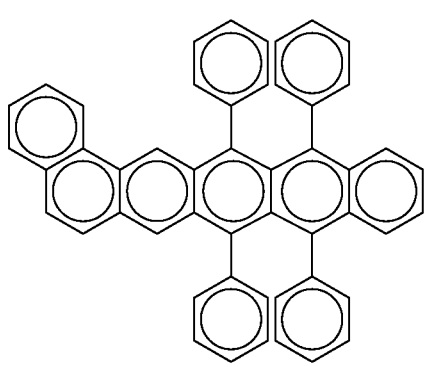
(A-23)
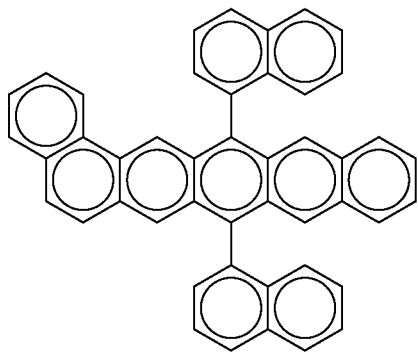

(A-24)

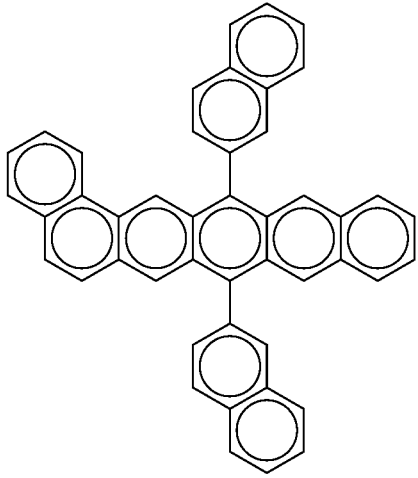

(A-25)

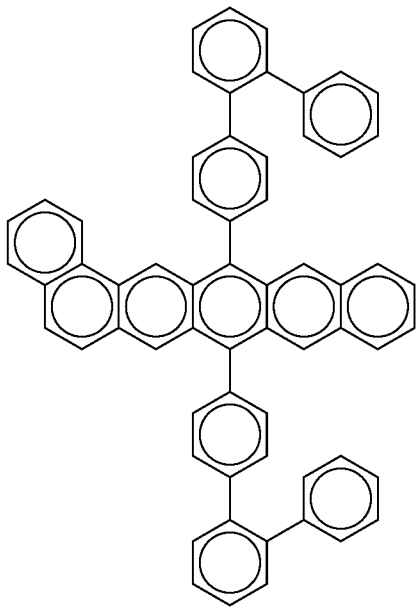

(A-26)

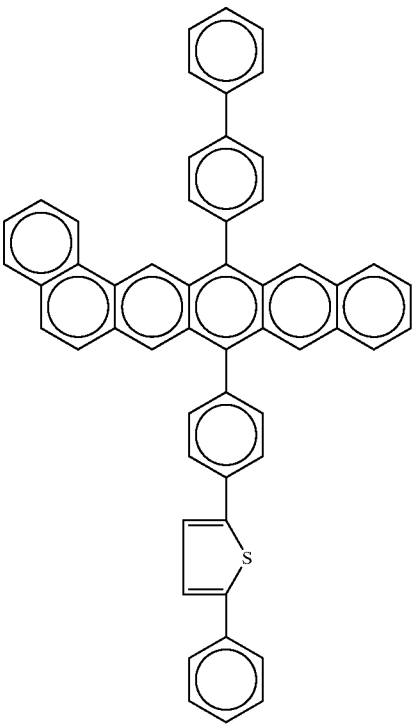

In the compound used in the organic EL device of the present invention, at least one pair of R among $R^1$ to $R^{14}$ which are adjacent to each other do not represent hydrogen atom but represent groups which form a cyclic structure in combination as described above. It is preferable that an unsaturated ring structure is formed in addition to the pentacene structure. Due to this structure, the organic EL device using this compound exhibits a more excellent efficiency of light emission and has a longer life than conventional devices do.

The organic EL device of the present invention is a device in which one or a plurality of organic thin films are disposed between an anode and a cathode. When the device has a single organic layer, a light emitting layer is disposed between an anode and a cathode. The light emitting layer contains a light emitting material and may also contain a hole injecting material to transport holes injected at the anode to the light emitting material or an electron injecting material to transport electrons injected at the cathode to the light emitting material. It is preferable that the light emitting layer is formed with a light emitting material having a very high quantum efficiency of fluorescence emission and excellent ability to transfer holes and electrons and a uniform thin film is formed. The organic EL device having a multi-layer structure has a laminate structure such as: (an anode/a hole injecting layer/a light emitting layer/a cathode), (an anode/a light emitting layer/an electron injecting layer/a cathode) and (an anode/a hole injecting layer/a light emitting layer/an electron injecting layer/a cathode).

In the light emitting layer, where necessary, conventional light emitting materials, doping materials, hole injecting materials and electron injecting materials may be used in addition to the compound represented by general formula [1], [2] or [2'] used in the present invention. Deterioration in the luminance and the life caused by quenching can be prevented by the multi-layer structure of the organic EL. Where necessary, light emitting materials, other doping materials, hole injecting materials and electron injecting materials may be used in combination. By using other doping materials, the luminance and the efficiency of light emission can be improved and red light and white light can be emitted. The hole injecting layer, the light emitting layer and the electron injecting layer may each have a multi-layer structure having two or more layers. When the hole injecting layer has a multi-layer structure, the layer into which holes are injected from the electrode is referred to as the hole injecting layer and the layer which receives holes from the hole injecting layer and transports holes from the hole injecting layer to the light emitting layer is referred to as the hole transporting layer. When the electron injecting layer has a multi-layer structure, the layer into which electrons are injected from the electrode is referred to as the electron injecting layer and the layer which receives electrons from the electron injecting layer and transports electrons from the electron injecting layer to the light emitting layer is referred to as the electron transporting layer. These layers are each selected and used in accordance with factors such as the energy level, heat resistance and adhesion with the organic layers or the metal electrodes of the material.

Examples of the material which can be used in the organic layer as the light emitting material or the host material in combination with the compound represented by general formula [1], [2] or [2'] include anthracene, naphthalene, phenanthrene, pyrene, tetracene, coronene, chrysene, fluoresceine, perylene, phthaloperylene, naphthaloperylene, perynone, phthaloperynone, naphthaloperynone, diphenylbutadiene, tetraphenylbutadiene, coumarine, oxadiazole, aldazine, bisbenzoxazoline, bisstyryl, pyrazine, cyclopentadiene, metal complexes of quinoline, metal complexes of aminoquinoline, metal complexes of benzoquinoline, imines, diphenylethylene, vinylanthracene, diaminocarbazole, pyrane, thiopyrane, polymethine, merocyanine, chelates of oxinoid compounds with imidazoles, quinacridone, rubrene, stilbene derivatives and fluorescent pigments. However, the above material is not limited to the compounds described above as the examples.

As the hole injecting material, a compound which has the ability to transfer holes, exhibits an excellent effect of hole injection from the anode and an excellent effect of hole injection to the light emitting layer or the light emitting material, prevents transfer of excited components formed in the light emitting layer into the electron injecting layer or the electron injecting material and has excellent ability to form a thin film is preferable. Examples of the above compound include phthalocyanine derivatives, naphthalocyanine derivatives, porphyrin derivatives, oxazole, oxadiazole, triazole, imidazole, imidazolone, imdazolethione, pyrazoline, pyrazolone, tetrahydroimidazole, oxazole, oxadiazole, hydrazone, acylhydrazone, polyarylalkanes, stilbene, butadiene, triphenylamines of the benzidine-type, triphenylamines of the styrylamine type, triphenylamines of the diamine type, derivatives of these compounds and macromolecular compounds such as polyvinylcarbazole, polysilane and conductive macromolecules. However, the above compound is not limited to the compounds described above as the examples.

Among the hole injection materials which can be used in the organic EL device of the present invention, aromatic tertiary amine derivatives and phthalocyanine derivatives are more effective.

Examples of the aromatic tertiary amine derivative include triphenylamine, tritolylamine, tolyldiphenylamine, N,N'-diphenyl-N,N'-(3-methylphenyl)-1,1'-biphenyl-4,4'-diamine, N,N, N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl) phenanthrene-9,10-diamine, N,N-bis(4-di-4-tolylaminophenyl)-4-phenylcyclohexane and oligomers and polymers having a skeleton structure of these aromatic tertiary amines. However, the aromatic tertiary amine derivative is not limited to the compounds described above as the examples.

Examples of the phthalocyanine (Pc) derivative include $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, GaPc-O-GaPc and corresponding derivatives of naphthalocyanine. However, the derivatives of phthalocyanine and naphthalocyanine are not limited to the compounds described above as the examples.

As the electron injecting material, a compound which has the ability to transport electrons, exhibits an excellent effect of electron injection from the cathode and an excellent effect of electron injection to the light emitting layer or the light emitting material, prevents transfer of excited components formed in the light emitting layer into the hole injecting layer and has excellent ability to form a thin film is preferable. Examples of the above compound include fluorenone, anthraquinodimethane, diphenoquinone, thiopyrane dioxide, oxazole, oxadiazole, triazole, imidazole, perylenetetracarboxylic acid, fluorenylidenemethane, anthraquinodimethane, anthrone and derivatives of these compounds. However, the above compound is not limited to the compounds described above as the examples. The charge injecting property can be improved by adding an electron accepting material to the hole injecting material or by adding an electron donating material to the electron injecting material.

In the organic EL device of the present invention, more effective electron injecting materials are metal complex compounds and five-membered derivatives containing nitrogen.

Examples of the metal complex compound include 8-hydroxyquinolinatolithium, bis(8-hydroxyquinolinato) zinc, bis(8-hydroxyquinolinato)copper, bis(8-hydroxyquinolinato)manganese, tris(8-hydroxyquinolinato) aluminum, tris(2-methyl-8-hydroxyquinolinato)-aluminum, tris(8-hydroxyquinilinato)gallium, bis(10-hydroxybenzo-[h] quinolinato)beryllium, bis(10-hydroxybenzo[h]quinolinato) zinc, bis(2-methyl-8-quinolinato)chlorogallium, bis(2-methyl-8-quinolinato) (o-cresolato)gallium, bis(2-methyl-8-quinolinato)(1-naphtholato)aluminum and bis(2-methyl-8-quinolinato)(2-naphtholato)gallium. However, the metal complex compound is not limited to the compounds described above as the examples.

Preferable examples of the five-membered derivative containing nitrogen include derivatives of oxazoles, thiazoles, thiadiazoles and triazoles. Specific examples include 2,5-bis (1-phenyl)-1,3,4-oxazole, dimethylPOPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'tert-butylphenyl)-5-(4"-biphenyl)-1,3,4-triazole, 2,5-bis(1-naphthyl)-1,3,4-triazole and 1,4-bis[2-(5-phenyltriazolyl)]benzene. However, the five-membered derivative containing nitrogen is not limited to the compounds described above as the examples.

In the organic EL device of the present invention, the organic layer may contain at least one of light emitting materials, doping materials, hole injecting materials and electron injecting materials in the same layer in addition to the compound represented by general formula [1], [2] or [2']. In order to improve stability of the organic EL device of the present invention with respect to temperature, humidity and oxygen, a protecting layer may be formed on the surface of the device or the entire device may be protected with silicon oil or a resin.

As the conductive material used for the anode of the organic EL device, a material having a work function of 4 eV or greater is suitable. Examples of such a material include carbon, aluminum, vanadium, iron, cobalt, nickel, tungsten, silver, gold, platinum, palladium, alloys of these metals, metal oxides used for ITO substrates and NESA substrates such as tin oxide and indium oxide and organic conductive resins such as polythiophene and polypyrrol. As the conductive material used for the cathode, a material having a work function smaller than 4 eV is suitable. Examples of such a material include magnesium, calcium, tin, lead, titanium, yttrium, lithium, ruthenium, manganese, aluminum and alloys of these metals. However, the materials used for the anode and the cathode are not limited to the materials described above as the examples. Typical examples of the alloy include alloys of magnesium and silver, alloys of magnesium and indium and alloys of lithium and aluminum. However, the alloy is not limited to these alloys described as the examples. The composition of the alloy is controlled by the temperature of the source of vapor deposition, the atmosphere and the degree of vacuum and can be adjusted suitably. The anode and the cathode may have a multi-layer structure having two or more layers, where necessary.

In the organic EL device, to achieve efficient light emission, it is preferable that at least one face of the device is sufficiently transparent in the wave length region of the emitted light. It is preferable that the substrate is also transparent. The transparent electrode is disposed in accordance with vapor deposition or sputtering using the above conductive material in a manner such that the prescribed transparency is surly obtained. It is preferable that the electrode disposed on the light emitting face has a transmittance of light of 10% or greater. The substrate is not particularly limited as long as the substrate has sufficient mechanical strength and strength at high temperatures and is transparent. Glass substrates or transparent films of resins may be used. Example of the transparent films of resins include films of polyethylene, ethylene-vinyl acetate copolymers, ethylene-vinyl alcohol copolymers, polypropylene, polystyrene, polymethyl methacrylate, polyvinyl chloride, polyvinyl alcohol, polyvinyl butyral, nylon, polyether ether ketones, polsulfones, polyether sulfones, tetrafluoroethylene-perfluoroalkyl vinyl ether copolymers, polyvinyl fluoride, tetrafluoroethylene-ethylene copolymers, tetrafluoroethylene-hexafluoropropylene copolymers, polychlorotrifluoro-ethylene, polyvinylidene fluoride, polyesters, polycarbonates, polyurethanes, polyether imides, polyimides and polypropylene.

Each layer of the organic EL device of the present invention can be formed suitably in accordance with a dry process of film formation such as vacuum vapor deposition, sputtering, plasma plating and ion plating or a wet process of film formation such as spin coating, dipping and flow coating. The thickness of the film is not particularly limited. However, it is necessary that the thickness be set at a suitable value. When the thickness is greater than the suitable value, a high voltage must be applied to obtain a prescribed output of light and the efficiency decreases. When the thickness is smaller than the suitable value, pin holes are formed and a sufficient luminance cannot be obtained even when the electric field is applied. In general, the suitable range of the thickness is 5 nm to 10 $\mu$m. A thickness in the range of 10 nm to 0.2 $\mu$m is preferable.

When the device is produced in accordance with a wet process, materials forming each layer are dissolved or dispersed in a suitable solvent such as ethanol, chloroform, tetrahydrofuran and dioxane and a film is formed from the solution or the suspension. The solvent is not particularly limited. In any organic thin layer, suitable resins and additives may be used to improve the property to form a film and to prevent formation of pin holes. Examples of the resin which can be used include insulating resins such as polystyrene, polycarbonates, polyarylates, polyesters, polyamides, polyurethanes, polysulfones, polymethyl methacrylate, polymethyl acrylate and cellulose, copolymers derived from these resins, photoconductive resins such as poly-N-vinylcarbazole and polysilane and conductive resins such as polythiophene and polypyrrol. Examples of the additive include antioxidants, ultraviolet light absorbents and plasticizers.

As described above, when the compound of the present invention is used for the organic layer of the organic EL device, the organic EL device exhibiting an excellent purity of color and a high efficiency of light emission, having a long life and emitting red light can be obtained.

The organic EL device of the present invention can be used for a planar light emitting member such as a flat panel display of wall televisions, a back light for copiers, printers and liquid crystal displays, a light source of instruments, display panels and a marker light.

The present invention will be described more specifically with reference to Synthesis Examples and Examples in the following.

Synthesis Example 1

(Compound A-1)

(1) Preparation of 1,2-bis(bromomethyl)naphthalene

In 300 ml of carbon tetrachloride, 10 g (64 mmole) of 1,2-dimethylnaphthalene and 46 g (260 mmole) of N-bromosuccinimide were suspended. To the obtained suspension, 1.7 g (260 mmole) of 2,2'-azobis(isobutyronitrile) was added and the mixture was vigorously stirred at 10° C. for 2 hours. After the reaction was completed, the reaction mixture was filtered and the residue was washed with 150 ml of dichloromethane. The filtrate and the washing were combined. The combined solution was treated by the column chromatography (silica gel/dichloromethane) without additional treatments and a white solid of 1,2-bis(bromomethyl)naphthalene was obtained in the quantitative amount.

The $^1$H-NMR spectrum of the product was obtained and the result was as follows:

$^1$H-NMR (CDCl$_3$, TMS) δ: 4.74 (2H, s), 4.98 (2H, s), 7.3–8.1 (6H, m)

(2) Preparation of 1-(bromomethyl)-2-(dibromomethyl)naphthalene

In 150 ml of carbon tetrachloride, 20 g (64 mmole) of 1,2-bis(bromomethyl)naphthalene and 23 g (130 mmole) of N-bromosuccinimide were suspended. To the obtained suspension, 1.1 g (6.7 mmole) of 2,2'-azobis (isobutyronitrile) was added and the mixture was vigorously stirred at 100° C. for 2 hours. After the reaction was completed, the reaction mixture was filtered and the residue was washed with 150 ml of dichloromethane. The filtrate and the washing were combined. The combined solution was treated by the column chromatography (silica gel/dichloromethane) without additional treatments and 16 g (the yield: 64%) of a white solid of 1-(bromomethyl)-2-(dibromomethyl)naphthalene was obtained.

The $^1$H-NMR spectrum of the product was obtained and the result was as follows:

$^1$H-NMR (CDCl$_3$, TMS) δ: 4.98 (2H, s), 7.27 (1H, s), 7.6–8.1 (6H, m)

(3) Preparation of 1,4-anthraquinone

In an atmosphere of argon, 60 g (550 mmole) of 1,4-benzoquinone, 100 g (240 mmole) of 1,2-bis(dibromomethyl)benzene and 235 g (1.6 mole) of sodium iodide were dissolved into 850 ml of dry dimethylformamide. After the exothermic reaction was completed, the reaction solution was heated to 70° C. and stirred for 8 hours. After the reaction was completed, the formed crystals were separated by filtration and washed with methanol and water and 23 g (the yield: 47%) of light yellow needle crystals of 1,4-anthraquinone were obtained.

The $^1$H-NMR spectrum of the product was obtained and the result was as follows:

$^1$H-NMR (CDCl$_3$, TMS) δ: 7.07 (2H, s), 7.6–8.1 (6H, m), 8.66 (2H, s)

(4) Preparation of 8,15-benzo[a]pentacenequinone

In an atmosphere of argon, 6.9 g (33 mmole) of 1,4-anthraquinone, 9.8 g (25 mmole) of 1-(bromomethyl)-2-(dibromomethyl)naphthalene and 25 g (660 mmole) of sodium iodide were dissolved into 85 ml of dry dimethylformamide. After the exothermic reaction was completed, the reaction solution was heated to 70° C. and stirred for 8 hours. After the reaction was completed, the formed crystals were separated by filtration and washed with methanol and water and light yellow needle crystals of 8,15-benzo[a]pentacenequinone were obtained in the quantitative amount.

The FD-MS (the field desorption mass spectrum) of the product was obtained and the result was as follows:

FD-MS: 358 (M$^+$)

(5) Preparation of 8,15-bis(p-biphenylyl)-8,15-dihydro-8,15-dihydroxy-benzo[a]pentacene In an argon atmosphere, 8.4 g (36 mmole) of 4-bromobiphenyl was dissolved into 100 ml of dry toluene and 50 ml of dry tetrahydrofuran and the obtained solution was cooled to −5° C. To the cooled solution, 24 ml of a n-hexane solution (1.52 mole/liter) of n-butyllithium was added dropwise and the solution was stirred for 1 hour. To the obtained reaction solution, 2.2 g (6.0 mmole) of 8,15-benzo[a]pentacenequinone in the solid form was added and the reaction mixture was stirred at the room temperature for 7 hours. After the reaction was completed, water was added to the reaction mixture. The organic layer was washed twice with water and once with a saturated aqueous solution of sodium chloride and dried with dry magnesium sulfate. Then, the solvents were removed and an oily product was obtained. The oily product was treated by the column chromatography (silica gel/hexane:dichloromethane=2:8 to 0:10) and 2.0 g (the yield: 51%) of a light yellow amorphous solid of 8,15-bis(p-biphenylyl)-8,15-dihydro-8,15-dihydroxybenzo[a]pentacene was obtained.

The $^1$H-NMR spectrum of the product was obtained and the result was as follows:

$^1$H-NMR (CDCl$_3$, TMS) δ: 6.73 (8H, dd), 6.9–8.1 (19H, m) 8.44 (2H, m), 8.70 (1H, m), 9.23 (1H, s)

(6) Preparation of 8,15-bis(p-biphenylyl)benzo[a] pentacene (Compound A-1)

In 150 ml of isopropyl ether and 75 ml of dichloromethane, 1.5 g (2.3 mmole) of 8,15-bis(p-biphenylyl)-8,15-dihydro-8,15-dihydroxybenzo[a]-pentacene was suspended. To the obtained suspension, 40 ml of a 57% aqueous solution of hydrogen iodide was added under the refluxing condition and the obtained mixture was stirred for 5 minutes. After the reaction was completed, the reaction solution was added to 500 ml of a saturated aqueous solution of sodium hydrogencarbonate and the obtained mixture was stirred for 10 minutes. The formed precipitates were separated by filtration and washed once with ion-exchanged water, once with a saturated aqueous solution of sodium disulfite and then three times with ion-exchanged water. The washed precipitates were dried under heating at a reduced pressure and 0.84 g (the yield: 51%) of a light purple solid of 8,15-bis(p-biphenylyl)benzo[a]pentacene was obtained. The obtained product was purified by sublimation at 320° C. under 4.0×10$^{-6}$ Torr for 2 hours and 450 mg of a deep purple amorphous solid was obtained.

The FD-MS of the product was obtained and the result was as follows:

FD-MS: 664 (MO$_2^+$, 38), 634 (M$^+$+1, 100)

The reaction to obtain Compound A-1 is shown in the following.

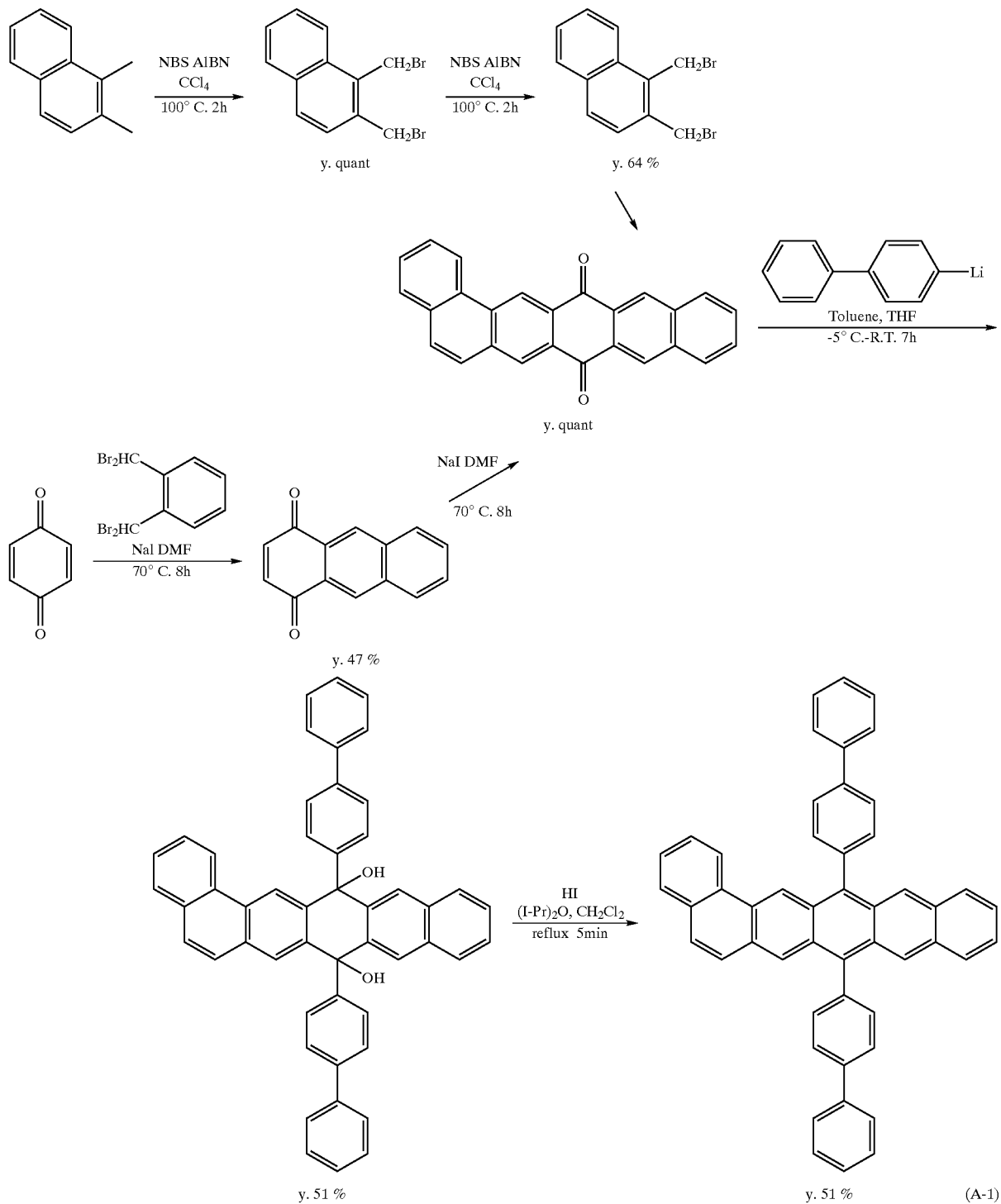

Synthesis Example 2
(Compound A-2)

(1) Preparation of 8,15-diphenyl-8,15-dihydro-8,15-dihydroxybenzo[a]-pentacene

In accordance with the same procedures as those conducted in Synthesis Example 1 (5) except that bromobenzene was used in place of 4-bromobiphenyl, a light yellow amorphous solid of 8,15-diphenyl-8,15-dihydro-8,15-dihydroxybenzo[a]pentacene was obtained.

The $^1$H-NMR spectrum of the product was obtained and the result was as follows:

$^1$H-NMR (CDCl$_3$, TMS) δ: 6.7–8.1 (19H, m) 8.44 (2H, m) 8.70 (1H, m), 9.23 (1H, s)

(2) Preparation of 8,15-diphenylbenzo[a]pentacene (Compound A-2)

In accordance with the same procedures as those conducted in Synthesis Example 1 (6) except that 8,15- diphenyl-8,15-dihydro-8,15-dihydroxybenzo[a]pentacene was used in place of 8,15-bis(p-biphenylyl)-8,15-dihydro-8,15-dihydroxybenzo[a]pentacene, a deep purple amorphous solid of 8,15-diphenylbenzo[a]pentacene was obtained.

The FD-MS of the product was obtained and the product was identified to be the object compound.

Synthesis Example 3
(Compound A-3)

(1) Preparation of 8,15-bis(m-biphenylyl)-8,15-dihydro-8,15-dihydroxy-benzo[a]pentacene In accordance with the same procedures as those conducted in Synthesis Example 1 (5) except that 3-bromobiphenyl was used in place of 4-bromobiphenyl, a light yellow amorphous solid of 8,15-bis(m-biphenylyl)-8,15-dihydro-8,15-dihydroxybenzo[a]pentacene was obtained.

(2) Preparation of 8,15-bis(m-biphenylyl)benzo[a]pentacene (Compound A-3)

In accordance with the same procedures as those conducted in Synthesis Example 1 (6) except that 8,15-bis(m-biphenylyl)-8,15-dihydro-8,15-dihydroxybenzo[a]pentacene was used in place of 8,15-bis(p-biphenylyl)-8,15-dihydro-8,15-dihydroxybenzo[a]pentacene, a deep purple amorphous solid of 8,15-bis(m-biphenylyl)benzo[a]pentacene was obtained.

The FD-MS of the product was obtained and the product was identified to be the object compound.

Synthesis Example 4
(Compound A-4)

(1) Preparation of 8,15-bis(o-biphenylyl)-8,15-dihydro-8,15-dihydroxy-benzo[a]pentacene In accordance with the same procedures as those conducted in Synthesis Example 1 (5) except that 2-bromobiphenyl was used in place of 4-bromobiphenyl, a light yellow amorphous solid of 8,15-bis(o-biphenylyl)-8,15-dihydro-8,15-dihydroxybenzo[a]pentacene was obtained.

(2) Preparation of 8,15-bis(o-biphenylyl)benzo[a]pentacene (Compound A-4)

In accordance with the same procedures as those conducted in Synthesis Example 1 (6) except that 8,15-bis(o-biphenylyl)-8,15-dihydro-8,15-dihydroxybenzo[a]pentacene was used in place of 8,15-bis(p-biphenylyl)-8,15-dihydro-8,15-dihydroxybenzo[a]pentacene, a deep purple amorphous solid of 8,15-bis(o-biphenylyl)benzo[a]pentacene was obtained.

The FD-MS of the product was obtained and the product was identified to be the object compound.

Synthesis Example 5
(Compound A-13)

(1) Preparation of (p-bromophenyl)diphenylamine

Into 500 ml of dry dimethylformamide, 50 g (200 mmole) of triphenylamine was dissolved. To the obtained solution, a solution prepared by dissolving 36 g (200 mmole) of N-bromosuccinimide into 100 ml of dry dimethylformamide was added and the obtained solution was stirred at the room temperature for 6 hours. After the reaction was completed, 1 liter of water was added to the reaction mixture and the formed precipitates were separated by filtration. The obtained light yellow solid was washed with water, dried at a reduced pressure and recrystallized from hexane and 38 g (the yield: 59%) of white needle crystals of the subject compound was obtained.

The $^1$H-NMR spectrum of the product was obtained and the result was as follows:

$^1$H-NMR (CDCl$_3$, TMS) δ: 6.9–7.4 (m)

(2) Preparation of 8,15-bis(p-diphenylaminophenyl)-8,15-dihydro-8,15-dihydroxybenzo[a]pentacene In accordance with the same procedures as those conducted in Synthesis Example 1 (5) except that (p-bromophenyl)diphenylamine was used in place of 4-bromobiphenyl, a light yellow amorphous solid of 8,15-bis(p-diphenylaminophenyl)-8,15-dihydro-8,15-dihydroxybenzo[a]pentacene was obtained.

(3) Preparation of 8,15-bis(p-diphenylaminophenyl)benzo[a]pentacene (Compound A-13)

In accordance with the same procedures as those conducted in Synthesis Example 1 (6) except that 8,15-bis(p-diphenylaminophenyl)-8,15-dihydro-8,15-dihydroxybenzo[a]pentacene was used in place of 8,15-bis(p-biphenylyl)-8,15-dihydro-8,15-dihydroxybenzo[a]pentacene, a purple amorphous solid of 8,15-bis(p-diphenylaminophenyl)benzo[a]pentacene was obtained.

The FD-MS of the product was obtained and the product was identified to be the object compound.

Synthesis Example 6
(Compound A-14)

(1) Preparation of 2,3-bis(bromomethyl)naphthalene

In accordance with the same procedures as those conducted in Synthesis Example 1 (1) except that 2,3-dimethylnaphthalene was used in place of 1,2-dimethylnaphthalene, a white solid of 2,3-bis(bromomethyl)-naphthalene was obtained in the quantitative amount.

(2) Preparation of 2-(bromomethyl)-3-(dibromomethyl)naphthalene

In accordance with the same procedures as those conducted in Synthesis Example 1 (2) except that 2,3-bis(bromomethyl)naphthalene was used in place of 1,2-bis(bromomethyl)naphthalene, a white solid of 2-(bromomethyl)-3-(dibromomethyl)naphthalene was obtained.

(3) Preparation of 1,4-tetracenequinone

In accordance with the same procedures as those conducted in Synthesis Example 1 (3) except that 2,3-bis(bromomethyl)naphthalene was used in place of 1,2-bis(dibromomethyl)benzene, a yellow solid of 1,4-tetracenequinone was obtained.

(4) Preparation of 8,17-benzo[a]hexacenequinone

In accordance with the same procedures as those conducted in Synthesis Example 1 (4) except that 2,3-bis(bromomethyl)naphthalene was used in place of 1,4- anthraquinone, a yellow solid of 8,17-benzo[a]-hexacenequinone was obtained.

(5) Preparation of 8,17-diphenyl-8,17-dihydro-8,17-dihydroxybenzo[a]-hexanone

In accordance with the same procedures as those conducted in Synthesis Example 1 (5) except that bromobenzene was used in place of 4-bromobiphenyl and 8,17-benzo[a]hexacenequinone was used in place of 8,15-benzo[a]pentacenequinone, a light yellow solid of 8,17-diphenyl-8,17-dihydro-8,17-dihydroxybenzo[a]hexanone was obtained.

(6) Preparation of 8,17-diphenylbenzo[a]pentacene (Compound A-14)

In accordance with the same procedures as those conducted in Synthesis Example 1 (6) except that 8,17-diphenyl-8,17-dihydro-8,17-dihydroxybenzo[a]hexanone was used in place of 8,15-bis(p-biphenylyl)-8,15-dihydro-8,15-dihydroxybenzo[a]pentacene, a black solid of 8,17-diphenylbenzo[a]pentacene was obtained.

The FD-MS of the product was obtained and the product was identified to be the object compound.

EXAMPLE 1

On a cleaned glass plate having an ITO electrode, the following compound (H232) as the hole injecting material was vapor deposited so that a film having a thickness of 60 nm was formed.

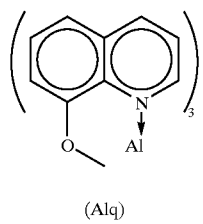

(Alq)

An electron injecting layer was formed by vapor deposition of Alq alone so that the formed film had a thickness of 10 nm. A layer of an inorganic compound was formed on the electron injecting layer by vapor deposition of LiF so that the formed film had a thickness of 0.2 nm. On the thus formed layer, aluminum was vapor deposited so that an electrode having a thickness of 170 nm was formed and an organic EL device was obtained. The vapor depositions for forming the above layers were conducted under $10^{-6}$ Torr while the substrate was kept at the room temperature.

The light emitting property of this device was as follows: the luminance under application of a direct current 7 V: 101 cd/m$^2$; and the efficiency of light emission: 2.64 cd/A. The emitted light was highly pure red light having chromaticity coordinates of (0.63, 0.37). When the device was driven under a constant current at an initial luminance of 500 cd/m$^2$, the half-life was as long as 1200 hours.

Comparative Example 1

An organic EL device was obtained in accordance with the same procedures as those conducted in Example 1 except

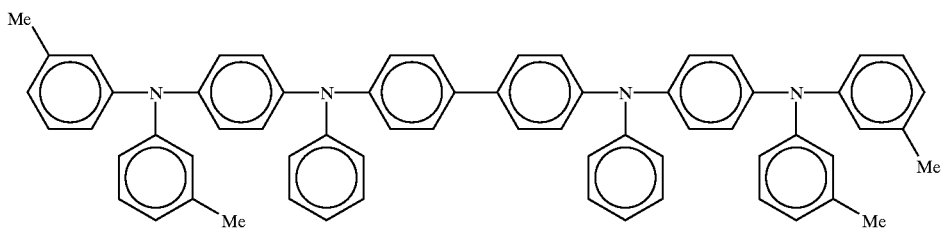

H 232

Then, the following compound (NPD) as the hole transporting material was vapor deposited so that a film having a thickness of 20 nm was formed.

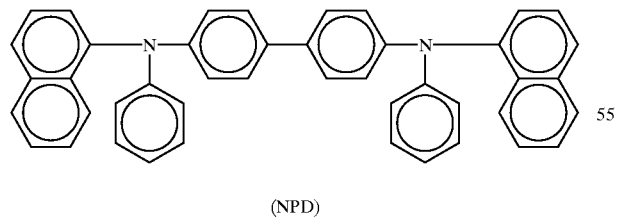

(NPD)

Subsequently, an aluminum complex of 8-hydroxyquinoline (Alq) and 8,15-bis(p-biphenylyl)benzo[a]pentacene (Compound A-1) as the materials for the light emitting layer were vapor deposited so that a film containing 1.8% by mole of Compound A-1 and having a thickness of 50 nm was formed. The structure of Alq is shown in the following:

that the compound shown below (Compound of Comparative Example 1) was vapor deposited in place of Compound A-1 so that the concentration of Compound of Comparative Example 1 was 2.0% by mole.

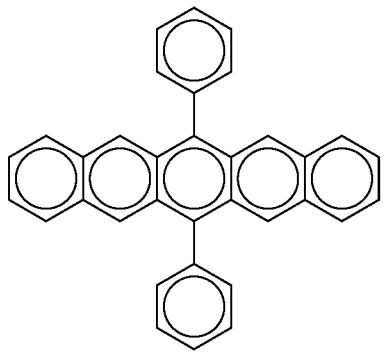

(Compound of Comparative Example 1)

The light emitting property of this device was as follows: the luminance under application of a direct current 11 V: 100 cd/m$^2$; and the efficiency of light emission: 0.3 cd/A. The voltage was higher by 4 V and the efficiency of light emission was lower than those of the device in Example 1. Although the emitted light was highly pure red light having chromaticity coordinates of (0.67, 0.32), the half-life was as short as 270 hours when the device was driven under a constant current at an initial luminance of 500 cd/m$^2$.

Comparative Example 2

An organic EL device was obtained in accordance with the same procedures as those conducted in Example 1 except that the compound shown below (DCJTB) which is a derivative of DCM was vapor deposited in place of Compound A-1 so that the concentration of DCJTB was 2.0% by mole.

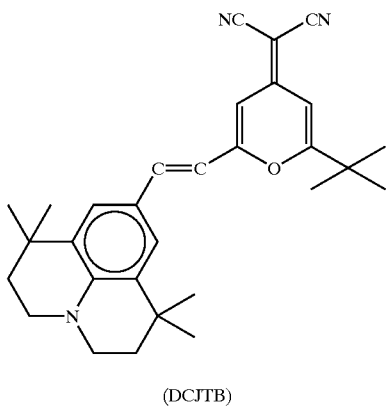

(DCJTB)

The light emitting property of this device was as follows: the luminance under application of a direct current 9 V: 91 cd/m$^2$; and the efficiency of light emission: 1.53 cd/A. The voltage was higher by 2 V and the efficiency of light emission was lower than those of the device in Example 1. Although the emitted light was highly pure red light having chromaticity coordinates of (0.65, 0.35), the half-life was as short as 120 hours when the device was driven under a constant current at an initial luminance of 500 cd/m$^2$.

EXAMPLE 2

An organic EL device was obtained in accordance with the same procedures as those conducted in Example 1 except that Compound A-3 was vapor deposited in place of Compound A-1 so that the concentration of Compound A-3 was 2.0% by mole.

The light emitting property of this device was as follows: the luminance under application of a direct current 7 V: 120 cd/m$^2$; and the efficiency of light emission: 3.26 cd/A. The emitted light was red light having chromaticity coordinates of (0.59, 0.39). The half-life was as long as 1000 hours when the device was driven under a constant current at an initial luminance of 500 cd/m$^2$.

EXAMPLE 3

An organic EL device was obtained in accordance with the same procedures as those conducted in Example 1 except that Compound A-22 was vapor deposited in place of Compound A-1 so that the concentration of Compound A-22 was 1.9% by mole.

The light emitting property of this device was as follows: the luminance under application of a direct current 7 V: 110 cd/m$^2$; and the efficiency of light emission: 2.5 cd/A. The emitted light was highly pure red light having chromaticity coordinates of (0.64, 0.33). The half-life was as long as 1600 hours when the device was driven under a constant current at an initial luminance of 500 cd/m$^2$.

Industrial Applicability

As described above in detail, the organic electroluminescence device of the present invention which utilizes the compound represented by general formula [1], [2] or [2'] emits reddish light, exhibits an excellent purity of color and a high efficiency of light emission and has a long life.

Therefore, the organic electroluminescence device of the present invention is advantageously used as a light source such as a planar light emitting member of televisions and a back light of displays.

What is claimed is:

1. An organic electroluminescence device which comprises an organic layer disposed between at least one pair of electrodes, wherein the organic layer comprises a compound represented by general formula [2]:

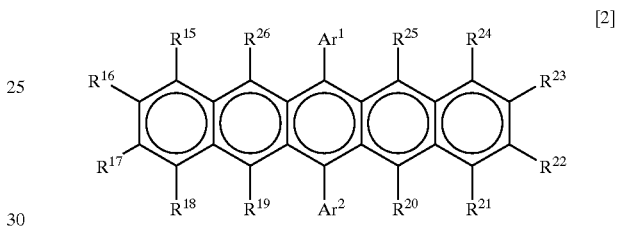

wherein $R^{17}$ to $R^{26}$ each independently represent hydrogen atom, an alkyl group having 1 to 10 carbon atoms, an aryloxy group having 6 to 20 carbon atoms, an arylalkyl group having 6 to 20 carbon atoms, an aryl group having 6 to 30 carbon atoms, an arylamino group having 6 to 30 carbon atoms, an alkylamino group having 2 to 20 carbon atoms or an arylalkylamino group having 6 to 30 carbon atoms, the groups being substituted or unsubstituted; wherein $R^{15}$ and $R^{16}$ represent groups which form a cyclic structure in combination and at least one additional pair of R among $R^{15}$ to $R^{26}$ which are adjacent to each other may represent groups which form a cyclic structure in combination; and $Ar^1$ and $Ar^2$ represent a substituted or unsubstituted aryl group having 6 to 30 carbon atoms or a substituted or unsubstituted heterocyclic group having 5 to 30 carbon atoms.

2. An organic electroluminescence device according to claim 1, wherein the organic layer comprises a light emitting layer which comprises the compound represented by general formula [2].

3. An organic electroluminescence device according to claim 2, wherein the light emitting layer comprises 0.1 to 20% by mole of the compound represented by general formula [2].

4. An organic electroluminescence device according to claim 2 or 3, wherein the light emitting layer has an electron transporting property.

5. An organic electroluminescence device according to claim 1, 2 or 3, wherein a layer of an inorganic compound is disposed between the organic layer and one of the electrodes of a pair of electrodes.

6. An organic electroluminescence device according to claim 1, 2 or 3, which emits reddish light.

7. The novel device claimed in claim 1, wherein the compound is 8,15-diphenylbenzo[a]pentacene.

8. A novel compound represented by general formula [2']:

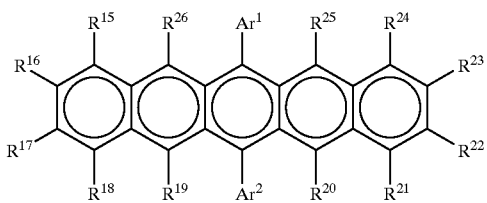

wherein $R^{17}$ to $R^{26}$ each independently represent hydrogen atom, an alkyl group having 1 to 10 carbon atoms, an aryloxy group having 6 to 20 carbon atoms, an arylalkyl group having 6 to 20 carbon atoms, an aryl group having 6 to 30 carbon atoms, an arylamino group having 6 to 30 carbon atoms, an alkylamino group having 2 to 20 carbon atoms or an arylalkylamino group having 6 to 30 carbon atoms, the groups being substituted or unsubstituted; wherein $R^{15}$ and $R^{16}$ represent groups which form a cyclic structure in combination and at least one additional pair of R among $R^{15}$ to $R^{26}$ which are adjacent to each other may represent groups which form a cyclic structure in combination; and $Ar^1$ and $Ar^2$ represent a substituted or unsubstituted aryl group having 6 to 30 carbon atoms or a substituted or unsubstituted heterocyclic group having 5 to 30 carbon atoms, excluding a case in which $Ar^1$ and $Ar^2$ both represent an unsubstituted phenyl group.

9. The novel compound claimed in claim 8, wherein the compound is 8,15-bis(p-biphenylyl)benzo[a]pentacene.

10. The novel compound claimed in claim 8, wherein the compound is 8,15-bis(m-biphenylyl)benzo[a]pentacene.

11. The novel compound claimed in claim 8, wherein the compound is 8,15-bis(o-biphenylyl)benzo[a]pentacene.

* * * * *